United States Patent
Ekwall et al.

[11] Patent Number: 6,016,443
[45] Date of Patent: Jan. 18, 2000

[54] IMPLANTABLE ISCHEMIA DETECTOR AND IMPLANTABLE STIMULATOR EMPLOYING SAME

[75] Inventors: Christer Ekwall, Spånga; Kjell Norén, Solna, both of Sweden

[73] Assignee: Pacesetter AB, Järfälla, Sweden

[21] Appl. No.: 09/048,521

[22] Filed: Mar. 26, 1998

[30] Foreign Application Priority Data

Mar. 26, 1997 [SE] Sweden .................................. 9701122

[51] Int. Cl.$^7$ ........................................................ A61B 5/04
[52] U.S. Cl. ........................................................ 600/519
[58] Field of Search .................................. 600/513, 515; 607/18

[56] References Cited

U.S. PATENT DOCUMENTS 4,228,803 10/1980 Rickards .
5,025,786 6/1991 Siegel .
5,065,759 11/1991 Begemann et al. ...................... 607/18
5,135,004 8/1992 Adams et al. .
5,269,301 12/1993 Cohen ...................... 607/18
5,330,511 7/1994 Boute .
5,531,768 7/1996 Alferness .

FOREIGN PATENT DOCUMENTS

WO 92/16257 10/1992 WIPO .

*Primary Examiner*—William E. Kamm
*Attorney, Agent, or Firm*—Hill & Simpson

[57] ABSTRACT

An ischemia detector includes repolarization sensor which senses repolarization of the heart of a patient and delivers corresponding repolarization signals to a detecting unit and a workload sensor which senses the workload of the patient and delivers corresponding workload signals to the detecting unit. The detecting unit identifies a state of ischemia as existing upon the occurrence of a predetermined relation between sensed repolarization and sensed workload.

19 Claims, 2 Drawing Sheets

IMPLANTABLE ISCHEMIA DETECTOR AND IMPLANTABLE STIMULATOR EMPLOYING SAME

BACKGROUND OF THE INVENTION

1. Field of the Invention

The present invention relates to an ischemia detector of the type wherein repolarization of the heart of a patient is sensed and corresponding repolarization signals are analyzed to detect an ischemic state (ischemic episode).

2. Description of the Prior Art

Ischemia is a condition resulting from insufficient blood flow through the heart muscle. The reason therefor is blocking or passage congestion of coronary blood vessels of the heart. An ischemic heart also loses its ability to adapt the heart blood flow to the demand, e.g. the workload. An ischemic episode is experienced by the patient as a severe chest pain and is one of the most stressing factors known to the organism and the patient is normally forced to sit down or lie down and feels the need for forced breathing, so called hyperventilation.

Compensatory effects will be activated to cope with the ischemic situation. Thus the heart rate will increase due to sympathetic nerve stimulation and increased catecholamines stimulation. In case of a limited or local ischemia this activation can compensate for the reduced capacity of a limited ischemic area of the heart.

In U.S. Pat. No. 5,199,428 a technique is described for detecting an ischemic episode and effecting stimulation of nerves regulating blood pressure and heart rate to reduce the heart's oxygen requirements while providing pacing therapies to maintain the patient's heart rate within acceptable limits to avoid bradyarrhythmias and/or unphysiological AV delays induced by the nerve stimulation. The ischemia detection is based on the occurrence of changes in the ST-segment variation different from predetermined or programmed threshold levels, or on changes in the pH and/or in the dissolved blood oxygen in venous return blood in the coronary sinus region of the patient's heart.

An ischemic state can also be detected by an analysis of recorded IECGs or surface ECGs to determine the heart rate variability. An ischemic state can be detected by a lead bending sensor located at the distal end portion of an implanted heart stimulator lead. Because the heart wall becomes thicker and stiffer as the result of ischemia, the accompanying change in the moving pattern of the heart wall can be detected in this way. Also, sound absorption is effected by changes in the stiffness of the heart tissue and by measuring the absorption of sound waves, generated e.g. at the heart valve closure, as they propagate from the upper portion of the ventricle to the apex region, an ischemic situation can be detected. An ischemic episode deteriorates the efficiency of the pumping of the heart and an ischemic situation therefore can be detected by studying blood pressures and cardiac outputs as well. Thus, by measuring the difference between the systolic and diastolic pressures and comparing this difference obtained from one heartbeat to the difference obtained from the next heartbeat an ischemic state can be detected. With the aid of a flow sensor for measuring cardiac output an ischemic state can be detected as well. An ischemic state also can be detected from the occurrence of the abnormal combination of a low workload and high breathing activity, which is typical of ischemic patients.

The onset of an increased heart rate related to an ischemic situation also can be detected from changes in the repolarization of the heart, such as changes in the QT interval, T-wave amplitude etc.

From U.S. Pat. No. 5,330,511 it is known to study variations in the QT-interval for determining an optimized AV-interval for a predetermined pacing rate for the control of a dual chamber pacemaker. The variation of the QT-interval is then studied as a function of the AV-delay for a fixed pacing rate and an optimum AV-interval is determined that interval which corresponds to the maximum QT. In U.S. Pat. No. 4,228,803 a physiologically adaptive cardiac pacemaker is disclosed having a circuitry for measuring the time interval between a stimulus pulse and the following T-wave. The escape interval of the pacemaker pulse generator is varied in accordance with the detected stimulus-to-T-wave interval so as to vary the pacing rate in accordance with this interval variation. Since this interval corresponds to physiological changes, the pacemaker is adapted to automatically follow the patient's physiological changes.

SUMMARY OF THE INVENTION

An object of the present invention is to provide a new type of ischemia detector, the function of which is based on the simultaneous detection of the onset of heart stress or increased heart rate and a low workload.

The above object is achieved in an ischemia detector in accordance with the invention having a repolarization sensor which senses repolarization of the heart of a patient and which delivers a signal indicative of the sensed repolarization to a detecting unit, and a workload sensor which senses the workload of the patient and which delivers a signal corresponding to the sensed workload to the detecting unit. The detecting unit identifies a state of ischemia upon the occurrence of a predetermined relation between the sensed repolarization and the sensed workload.

The ischemia detector according to the invention thus employs a workload sensor for sensing the workload of the patient and a repolarization sensor for sensing repolarization changes which are characteristic of the onset of heart stress.

According to various embodiments of the detector of the invention, the workload sensor can be an activity sensor for sensing an activity parameter of the patient, like body movements, muscular sounds or pressure waves in body fluids due to the work load of the patient, or a sensor for sensing metabolic changes, like changes in nutrition and oxygen consumption of the patient.

In other embodiments of the ischemia detector according to the invention, the repolarization sensor can be a time measuring unit for determining the QT time interval between the onset of the QRS complex and a predetermined point on the T-wave, detected by the repolarization sensor, the detector identifying a state of ischemia as existing upon the occurrence of a predetermined relation between the time interval and the sensed workload. The predetermined point on the T-wave is preferably selected on the rear slope of the T-wave. Repolarization in ischemic tissue is prolonged and the T-wave is deformed, especially on the leading slope. The rear slope of the T-wave remains, however, substantially unchanged and therefore it is appropriate to select the measuring point for the QT-time interval determination to be a point on the rear slope of the T-wave.

In another embodiment of the detector according to the invention, the detector includes an averaging unit which forms an average value of repolarization signals from a predetermined number of cardiac cycles to form an average repolarization signal representing the repolarization used for the detection of an ischemia. In this way influences from momentary variations due to e.g. breathing, position changes of the patient etc., are reduced.

According to another embodiment of the inventive ischemia detector, an alerting indicator is provided which is activated in response to a detected ischemic state. This is of particular value to patients having so-called silent ischemia, the occurrence of which the patient otherwise would not be aware of. When being alerted the patient may suitably lower his or her activity.

According to another aspect of the invention an implantable heart stimulator is provided having means for varying the stimulation rate and an ischemia detector.

In this inventive heart stimulator, control means are connected to the ischemia detector for controlling the stimulation rate varying means in response to the detection of an ischemia. Thus by lowering the stimulation rate at an early stage of an ischemia the further development thereof can be inhibited.

DESCRIPTION OF THE PREFERRED EMBODIMENTS

Figure 1:
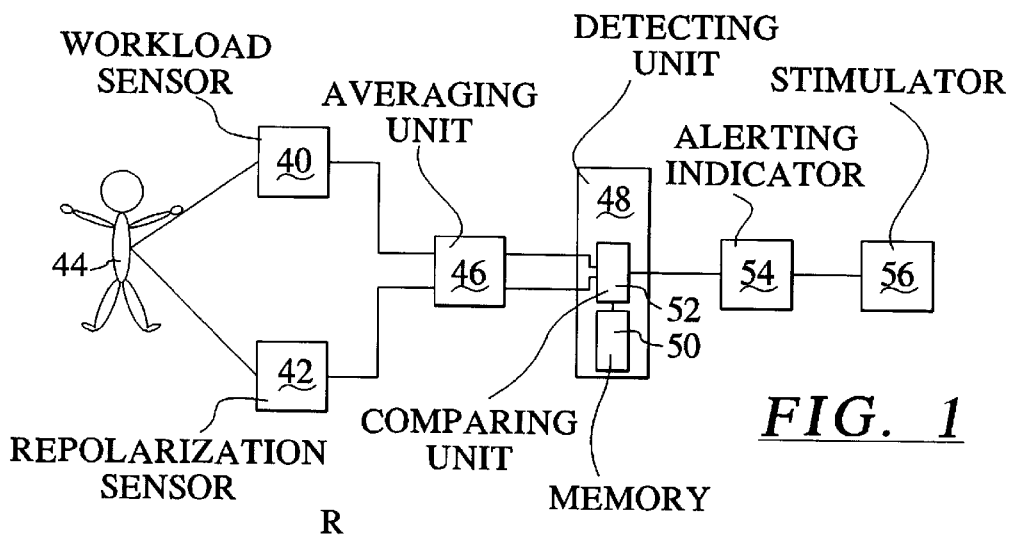
FIG. 1 is a block diagram of an embodiment of an ischemia detector according to the invention.

In FIG. 1 a workload sensor 40 and a repolarization sensor 42 are disposed for sensing the workload and the repolarization respectively of the heart of a patient 44. The sensors 40 and 42 deliver respective signals (shown in FIG. 6) to an averaging unit 46, in which averaged values for time periods of predetermined lengths are formed of the workload and repolarization signals. These averaged signal values are supplied to detecting unit 48.

The detecting unit 48 has a memory 50, in which one or more relations between repolarization and workload are stored, and a comparing unit 52, in which the relation between the signals from the averaging unit 46 representing sensed workload and repolarization is compared to the predetermined relations stored in the memory 50.

When a predetermined relation between the signals from the averaging unit 46 is detected an alerting means 54 connected to the comparing unit 52 is triggered to provide a humanly perceptible indication of the occurrence of an ischemic state. The heart stimulator 56 is connected to the alerting indicator 54 for changing, normally lowering, the stimulation rate in response to the detection of an ischemic state, as will be described more in detail below.

The workload sensor 40 can be an activity sensor, e.g. an accelerometer, for sensing body movements of the patient or a sensor for sensing muscular sounds or pressure waves in body fluids of the patient. Alternatively, the workload sensor 40 can be any type of sensor for sensing metabolic changes, like changes in nutrition and oxygen consumption of the patient.

Figure 2:
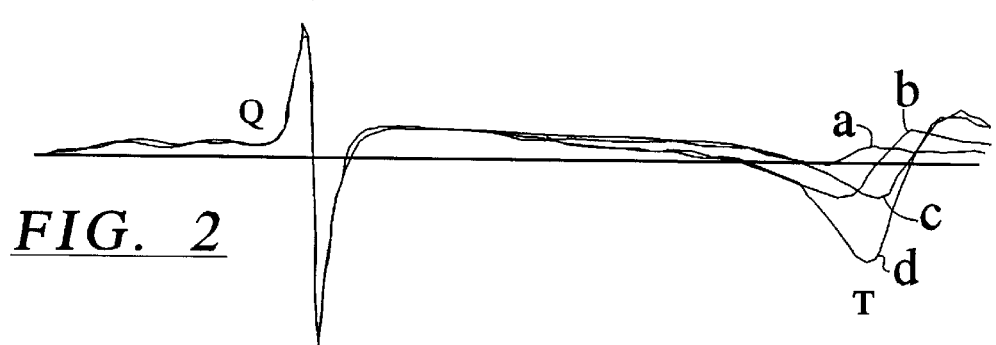
FIG. 2 shows IEGMs recorded in the ventricle and illustrating changes in the T-wave region associated with an ischemic state.

The repolarization sensor 42 can be disposed to determine the magnitude of a characteristic portion of the T-wave, e.g. the T-wave amplitude or width. Repolarization in ischemic tissue is prolonged and the T-wave is deformed, the polarity of the T-wave can even be reversed, and the onset of increased heart rate due to ischemic stress results in an increased T-wave amplitude, cf FIG. 2, which shows an IEGM a recorded in the ventricle before an ischemic episode, an IEGM b during induced ischemia, and IEGMs c and d at respectively different times after removal of the occlusion inducing the ischemia. As can be seen from FIG. 2, the T-wave is deformed when an ischemic situation occurs, but the rear slope of the T-wave remains well-defined and the repolarization sensor 42 therefore can include a time measuring arrangement for determining the QT-time interval between the onset of the QRS-complex and a predetermined point on the rear slope of the T-wave, this QT-time interval being shortened when an ischemic state develops.

As an alternative, the repolarization sensor 42 can determine the amplitude of the T-wave, the T-wave amplitude increasing in an ischemic situation.

Figure 3:
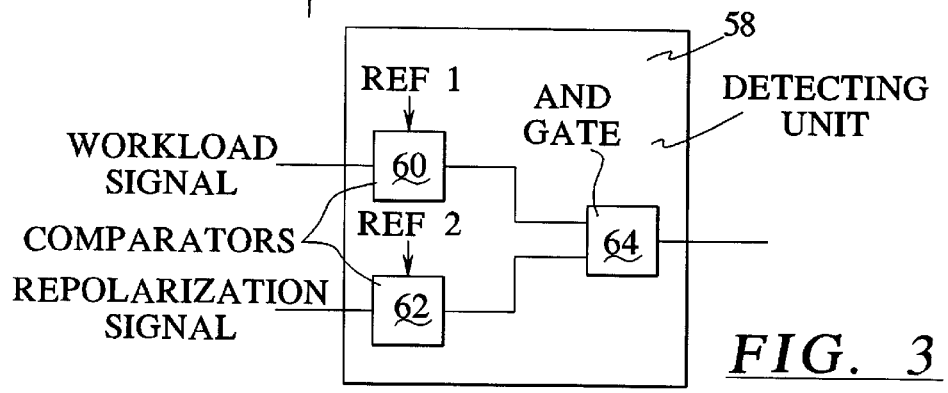
FIG. 3 is a block diagram illustrating one specific realization of the operation of the detector according to the invention.

An alternative embodiment of the detecting unit is shown in FIG. 3. In this embodiment the detecting unit 58 contains two comparators 60, 62 to which the workload signal and the repolarization signal are supplied respectively for comparison of the signals with predetermined threshold values Ref 1 and Ref 2. The repolarization signal can then represent e.g. the amplitude of the T-wave or the length of the QT-time interval as described above, the threshold value Ref 2 then being a predetermined amplitude threshold value or a predetermined QT-time interval limit. The outputs of the comparators 60, 62 are connected to the inputs of an AND-gate 64.

Figure 6:
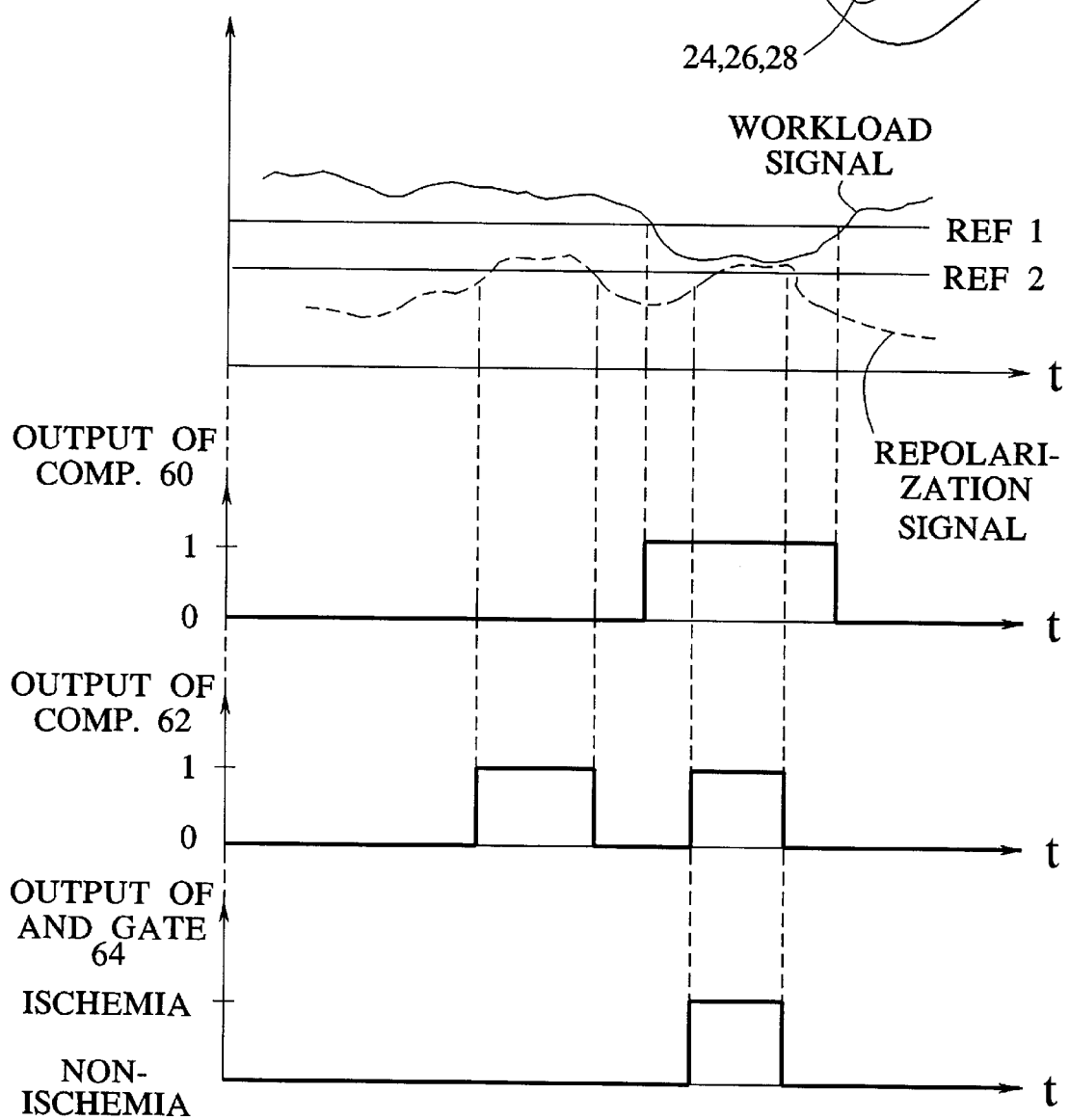
FIG. 6 shows examples of the workload signal and the repolarization signal, relative to respective reference signals, as well as the respective outputs of the comparators and the AND gate shown in FIG. 3.

As described above the occurrence of onset of an increased heart rate, detected from the repolarization of the heart, without a corresponding sensed increased workload, is identified as an ischemic situation. As shown in FIG. 6, the comparator 60 is thus arranged to deliver an output signal when the workload signal is below the predetermined workload threshold value Ref 1 and the comparator 62 delivers an output signal if the repolarization signal in the form of the peak amplitude of the T-wave is above the threshold value Ref 2 or QT-time interval is shorter than the QT-time interval limit Ref 2. In this case an output signal is obtained from the AND-gate 64 for e.g. activation of ischemia alerting indicator 54 and possible control of the stimulation rate of a heart stimulator.

Figure 4:
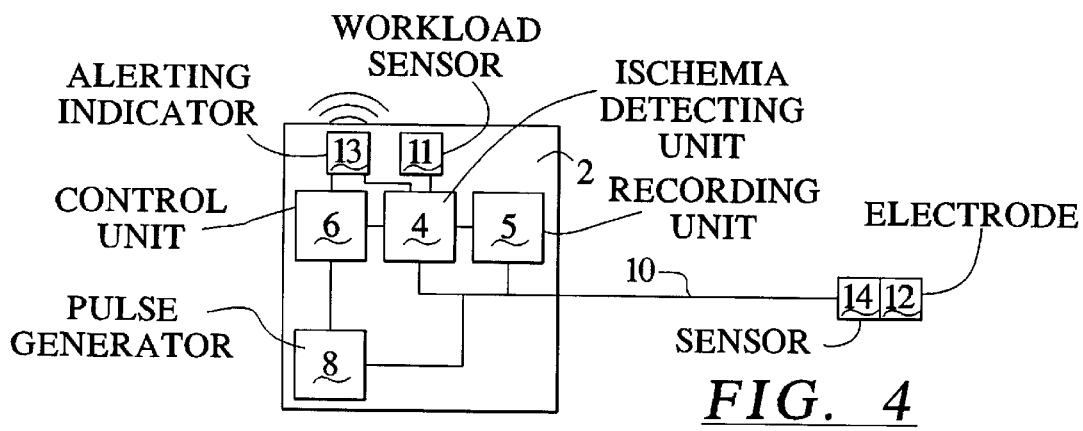
FIG. 4 is a simplified block diagram of one embodiment of a heart stimulator according to the invention.

FIG. 4 is a simplified block diagram of an implantable heart stimulator 2 according to the invention. The heart stimulator 2 has an ischemia detecting arrangement including an ischemia detecting unit 4, and a control unit 6, connected to the ischemia detecting unit 4. The control unit 6 is also connected to a pulse generator 8 for controlling the rate of generated stimulation pulses. The pulse generator 8 is connected to a lead 10 provided with electrodes 12 at the distal end portion for delivery of stimulation pulses and for possible electrical measurements. The lead 10 is intended to be implanted into the heart of the patient, preferably with the electrodes 12 in the right ventricle, cf FIG. 5. A sensor 14 is also provided at the distal end portion of the lead 10, and sensed signals are supplied therefrom to the ischemia detecting unit 4 through the lead 10.

The sensor 14 can be used for recording IECGs and may include electrodes as will be described in connection with FIG. 5. The signals are supplied by the lead 10 to an IECG recording unit 5, in which e.g. the magnitude of a characteristic portion of the T-wave, like the T-wave peak amplitude, or the QT-time interval, is determined and a corresponding output signal is delivered to the ischemia detecting unit 4.

A workload sensor 11 of any suitable kind mentioned above is also provided in the heart stimulator 2.

The heart stimulator 2 is also provided with an alerting indicator 13, e.g. a wrist watch "beeper-type". The alerting indicator 13 is connected to the ischemia detecting unit 4 to be activated when the predetermined relation occurs between the repolarization signal received from the unit 5 and the workload signal received from the workload sensor 11, indicating the presence of an ischemic situation. Alternatively the alerting indicator 13 can be connected to the control unit 6 to be activated when the stimulation rate is lowered as a result of a detected ischemic state. The alerting indicator 13 is of particular value for patients having "silent" ischemia, the occurrence of which the patient otherwise would not be aware.

Figure 5:
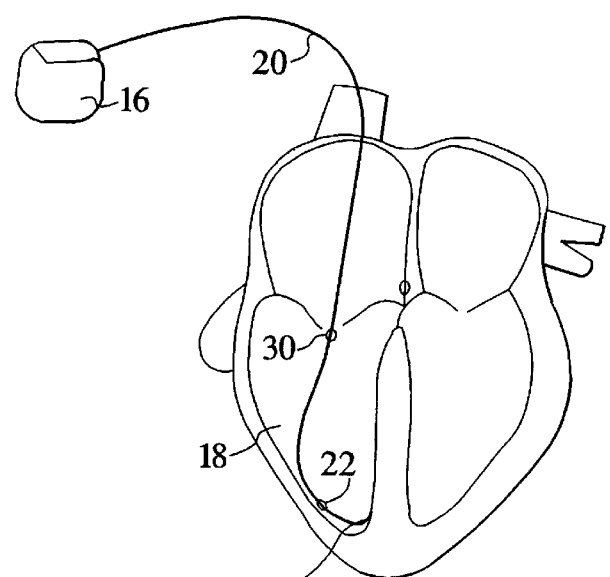
FIG. 5 shows a pacemaker, such as the heart stimulator of FIG. 4, with its lead implanted in the right ventricle of a heart.

FIG. 5 shows an implanted heart stimulator in the form of a pacemaker 16, connected to the right ventricle 18 of the heart of a patient by the pacemaker lead 20, which is of a bipolar type with an electrode ring 22 and a tip electrode 24. The lead 20 is also provided with electrodes 26, 28, e.g. electrodes for recording IECGs, as mentioned above.

As an alternative, the electrodes 26, 28 can be used to determine e.g. both the T-wave amplitude and the QT-time interval and deliver an output signal from the comparator 62 that will be produced only when both the T-wave amplitude and the QT-time interval fulfil their predetermined ischemia conditions.

An important advantage of the present invention is that a conventional cardiac electrode system can be used for detecting the changes in the repolarization or, if separate sensing means are used, these can be mounted on the lead intended to be implanted into the patient's heart for stimulation purposes.

The stimulation rate of the heart stimulator 16 is reduced in response to ischemia detector, detected as described above. There are different possibilities of reducing the stimulation rate. The control unit 6 can inhibit the delivery of a particular stimulation pulse, thus temporarily producing a longer interval between two consecutive pulses. The control unit 6 can also be arranged to more regularly inhibit a stimulation pulse out of a specified number of stimulation pulses in response to a detected ischemia. As a further alternative the control unit 6 can be arranged to control the pulse generator 8 such that the stimulation rate is uniformly reduced on the detection of an ischemia, or the stimulation rate can be shifted to selected lower rates.

Although modifications and changes may be suggested by those skilled in the art, it is the intention of the inventors to embody within the patent warranted hereon all changes and modifications as reasonably and properly come within the scope of their contribution to the art.

We claim as our invention:

1. An ischemia detector comprising:
   repolarization sensing means for measuring a magnitude of a characteristic portion of a T-wave of a heart of a patient and for generating a first signal indicative of said magnitude;
   workload sensing means for sensing a workload of a patient and for generating a second signal indicative of sensed workload; and
   detecting means, supplied with said first and second signals, for identifying a state of ischemia upon an occurrence of a predetermined relation between the magnitude and the sensed workload.

2. An ischemia detector as claimed in claim 1 wherein said workload sensing means comprise an activity sensor which senses an activity parameter of a patient.

3. An ischemia detector as claimed in claim 2 wherein said activity sensor comprises a sensor selected from the group consisting of a body movement sensor, a muscular sound sensor and a sensor which measures pressure waves in a body fluid.

4. An ischemia detector as claimed in claim 1 wherein said workload sensing means comprise a sensor which senses metabolic changes.

5. An ischemia detector as claimed in claim 4 wherein said sensor which senses metabolic changes comprises a sensor selected from the group consisting of a nutrition change sensor and an oxygen consumption change sensor.

6. An ischemia detector as claimed in claim 1 further comprising indicator means, connected to said detector means, for producing a humanly perceptible indication upon an identification of a state of ischemia by said detecting means.

7. An ischemia detector comprising:
   repolarization sensing means for measuring an amplitude of a T-wave of a heart of a patient and for generating a first signal indicative of said amplitude;
   workload sensing means for sensing a workload of a patient and for generating a second signal indicative of sensed workload; and
   detecting means, supplied with said first and second signals, for identifying a state of ischemia upon an occurrence of a predetermined relation between the amplitude and the sensed workload.

8. An ischemia detector as claimed in claim 7 wherein said activity sensor comprises a sensor selected from the group consisting of a body movement sensor, a muscular sound sensor and a sensor which measures pressure waves in a body fluid.

9. An ischemia detector as claimed in claim 8 wherein said activity sensor comprises a sensor selected from the group consisting of a body movement sensor, a muscular sound sensor and a sensor which measures pressure waves in a body fluid.

10. An ischemia detector as claimed in claim 7 wherein said workload sensing means comprise a sensor which senses metabolic changes.

11. An ischemia detector as claimed in claim 10 wherein said sensor which senses metabolic changes comprises a sensor selected from the group consisting of a nutrition change sensor and an oxygen consumption sensor.

12. An ischemia detector as claimed in claim 7 further comprising indicator means, connected to said detector means, for producing a humanly perceptible indication upon an identification of a state of ischemia by said detecting means.

13. An ischemia detector as claimed in claim 7 wherein said detecting means comprise means for detecting said state of ischemia upon said sensed workload being below a predetermined workload threshold and a simultaneously sensed T-wave amplitude exceeding a predetermined amplitude threshold.

14. An ischemia detector comprising:
   repolarization sensing means for sensing repolarization of a heart of a patient in a predetermined number of cardiac cycles, and in each of said cardiac cycles generating a first signal indicative of sensed repolarization, thereby producing a plurality of first signals;

workload sensing means for sensing a workload of a patient and for generating a second signal indicative of sensed workload;

an averaging unit supplied with said plurality of first signals, which forms an average repolarization signal as an average of said plurality of first signals; and detecting means, supplied with said average repolarization signal and said second signal, for identifying a state of ischemia upon an occurrence of a predetermined relation between said average repolarization signal and the sensed workload.

15. An ischemia detector as claimed in claim 14 wherein said workload sensing means comprise an activity sensor which senses an activity parameter of a patient.

16. An ischemia detector as claimed in claim 15 wherein said activity sensor comprises a sensor selected from the group consisting of a body movement sensor, a muscular sound sensor and a sensor which measures pressure waves in a body fluid.

17. An ischemia detector as claimed in claim 14 wherein said workload sensing means comprise a sensor which senses metabolic changes.

18. An ischemia detector as claimed in claim 17 wherein said sensor which senses metabolic changes comprises a sensor selected from the group consisting of a nutrition change sensor and an oxygen consumption change sensor.

19. An ischemia detector as claimed in claim 14 further comprising indicator means, connected to said detector means, for producing a humanly perceptible indication upon an identification of a state of ischemia by said detecting means.

* * * * *